(12) United States Patent
Luebbert et al.

(10) Patent No.: US 7,712,348 B2
(45) Date of Patent: May 11, 2010

(54) DEVICE AND METHOD FOR THE SELECTIVE DETERMINATION OF THE QUANTITY OF OIL MIST

(75) Inventors: Christian Luebbert, Cottbus (DE); Harald Heyer, Wesenberg (DE); Andreas Mohrmann, Krummesse (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 328 days.

(21) Appl. No.: 11/733,823

(22) Filed: Apr. 11, 2007

(65) Prior Publication Data
US 2007/0266769 A1 Nov. 22, 2007

(30) Foreign Application Priority Data
May 19, 2006 (DE) ............... 10 2006 023 714

(51) Int. Cl.
*G01N 1/22* (2006.01)
*G01N 21/00* (2006.01)
*G01N 33/26* (2006.01)

(52) U.S. Cl. .............. 73/29.04; 73/28.01; 422/55

(58) Field of Classification Search ........... 73/28.05, 73/863.22, 863.41, 863.51, 863.52, 863.53, 73/864.71, 863.72; 250/282–284, 301; 436/159
See application file for complete search history.

(56) References Cited

U.S. PATENT DOCUMENTS

| 2,622,471 | A | * | 12/1952 | Sparks | 73/53.06 |
|---|---|---|---|---|---|
| 3,561,253 | A | * | 2/1971 | Frank | 73/24.03 |
| 4,004,453 | A | * | 1/1977 | Thyrum | 73/61.59 |
| 4,133,202 | A | * | 1/1979 | Marple | 73/28.06 |
| 4,213,044 | A | | 7/1980 | Perrotta | |
| 4,460,544 | A | * | 7/1984 | Leichnitz | 422/59 |
| 4,590,792 | A | | 5/1986 | Chiang | |

FOREIGN PATENT DOCUMENTS

| DE | 32 23 742 C2 | 1/1985 |
|---|---|---|
| DE | 3937343 | 5/1991 |
| GB | 2122344 | 1/1984 |
| JP | 61117431 | 6/1986 |
| JP | 2005203559 | 7/2005 |
| JP | 2005249038 | 9/2005 |
| WO | WO 03/089907 | 10/2003 |

OTHER PUBLICATIONS

"Baffle". Webster's Third New Internation Dictionary, Unabridged, Copyright 1993. Merriam-Webster, Inc.*

(Continued)

*Primary Examiner*—Lisa M Caputo
*Assistant Examiner*—Punam Patel
(74) *Attorney, Agent, or Firm*—McGlew and Tuttle, P.C.

(57) ABSTRACT

A device for the selective determination of the quantity of oil mist includes an impactor (1) with a micronozzle (4) for dispensing a predetermined volume of a gas to be tested, a baffle plate (5) arranged downstream of the micronozzle (4) for depositing oil particles. A window (7) is provided on the side of the baffle plate (5) facing away from the micronozzle (4).

11 Claims, 6 Drawing Sheets

U.S. PATENT DOCUMENTS

| | | | |
|---|---|---|---|
| 4,936,016 A * | 6/1990 | Simpson | 73/61.62 |
| 5,553,795 A * | 9/1996 | Tsai et al. | 241/40 |
| 6,000,394 A * | 12/1999 | Blaha-Schnabel et al. | 128/200.19 |
| 6,156,212 A | 12/2000 | Rader et al. | |
| 6,972,841 B2 * | 12/2005 | Krempl et al. | 356/338 |
| 2005/0247868 A1 | 11/2005 | Call et al. | |
| 2008/0048108 A1 * | 2/2008 | Barkus | 250/282 |

OTHER PUBLICATIONS

"Baffle plate". Webster's Third New Internation Dictionary, Unabridged, Copyright 1993. Merriam-Webster, Inc.*

V. A. Marple, "History of Impactors-The First 110 Years." Aerosol Science and Technology, vol. 38, Issue 3, pp. 247-292, Mar. 1, 2004.*

Window. (1993). In Webster's Thrid New International Dictionary, Unabridged. Retrieved from <http://lionreference.chadwyck.com> on Sep. 14, 2009.*

* cited by examiner

DEVICE AND METHOD FOR THE SELECTIVE DETERMINATION OF THE QUANTITY OF OIL MIST

CROSS REFERENCE TO RELATED APPLICATIONS

This application claims the benefit of priority under 35 U.S.C. §119 of German Patent Application DE 10 2006 023 714.5 filed May 19, 2006, the entire contents of which are incorporated herein by reference.

FIELD OF THE INVENTION

The present invention pertains to a device and to a method for the selective determination of the quantity of oil mist.

BACKGROUND OF THE INVENTION

A gas detector tube for determining the quantity of oil mist in a gas sample has become known from DE 32 23 742 C2. A certain test gas volume is first drawn by means of a pump through the gas detector tube and the oil mist present in the test gas is deposited on a filter within the gas detector tube. An ampule containing sulfuric acid is then pierced, as a result of which the oil in the filter is dissolved and rinsed into a display layer via a distributor layer. A color display, which is proportional to the quantity of the oil mist filtered out of the test gas, is formed in the display layer.

The drawback of the prior-art gas detector tube is that a color chart is needed for the evaluation of the display in order to make it possible to state the quantity of oil mist. Such a color comparison is not always unambiguous and also depends on the user's individual color perception.

SUMMARY OF THE INVENTION

The basic object of the present invention is to propose a device and a method for the selective measurement of the quantity of oil mist in a gas sample, which is easy to handle and makes do without a chemical detection reaction.

According to the invention, a device is provided for the selective determination of the quantity of oil mist in a gas sample. The device includes an impactor with a micronozzle for dispensing a predetermined volume of gas to be tested as well as a baffle plate downstream of the micronozzle for depositing oil particles from the sample. An evaluating means is provided in the area of the baffle plate.

The evaluating means or evaluating device may be provided comprising a window provided on a side of the baffle plate facing away from the micronozzle.

The baffle plate may advantageously be provided comprising a frosted glass.

The baffle plate may advantageously be provided with an absorbent material as the evaluating means downstream of the micronozzle.

The evaluating means or evaluating device may be provided including a scale in the area of the window for determining an aerosol limit value.

A plurality of micronozzles may advantageously be arranged in a predetermined pattern. The pattern may advantageously be a circle, a square, a rectangle, a triangle, a symbol or a letter.

A critical nozzle (throttle or flow restriction) may advantageously be arranged downstream of said micronozzle of the impactor.

The evaluating means or evaluating device may advantageously comprise a capacitor which changes its capacity due to the oil particles. The capacitor may be employed as a frequency-determining component of an electric oscillatory circuit.

The evaluating device or evaluating means may advantageously comprise a capillary receiving the oil, an electrode array for conductivity measurement, or an optical image converter in the form of a charge couple device (CCD) chip.

According to another aspect of the invention, a method is provided for the selective determination of a quantity of oil mist in a gas sample. The method includes dispensing a predetermined volume of gas to be tested with a micronozzle and depositing oil particles on a baffle plate arranged downstream of the micronozzle according to the impactor principle. The method further includes determining a quantity of deposited oil particles with an evaluating device in the area of the baffle plate.

The method may advantageously use a window for providing the evaluating means. The window may be arranged on the side of the baffle plate facing away from the micronozzle.

The advantage of the present invention is essentially that due to the use of an impactor, the oil particles to be detected no longer follow the flow because of the abruptly changing flow, but are deposited on a baffle plate and collected. The quantity of the oil particles collected during a predetermined measurement time is an indicator of the oil content in the gas sample. The device according to the present invention and the method are generally suitable for the detection of liquids with very low vapor pressure.

The quantity of oil deposited can be determined in an especially simple manner via a window at the baffle plate by the direct evaluation of the size of an oil spot. The baffle plate either consists for this purpose of ground or etched glass or is provided with an absorbent material, which absorbs the oil. Even very small quantities of oil, for example, <10 μg, can thus be determined visually. The diameter of the oil spot can be evaluated in the simplest case by means of a scale. By using optical aids, for example, a magnifying glass, it is possible to evaluate even very small oil spots. The scale can be embodied by applying a printed ring, or there is a length display within the window. The oil spot is easy to see on ground or etched glass because the tiny depressions of the ground glass, which scatter light, are filled by oil particles. The glass again becomes transparent as a result because the refractive index has changed.

An increase in sensitivity and a shortening of the measurement time can also be achieved, for example, by a directed parallel connection of different impactors. It is especially advantageous for this to arrange a plurality of micronozzles in a predetermined pattern opposite the baffle plate. Such a pattern may be, for example, a circle, a square, a rectangle, a triangle, a symbol or a letter. Many small oil spots will be formed as a result on the baffle plate, and they will later merge into a single spot. It is possible here in the form of a threshold value calibration to determine the point in time at which the oil spots come into contact with one another.

A further improvement of the sensitivity of measurement is achieved by a critical nozzle being arranged downstream of the micronozzle of the impactor. Defined pressure ratios are obtained as a result within the impactor housing, and expansion of the gas jet exiting from the micronozzle can be avoided. This is of particular advantage especially when a plurality of micronozzles are used within the impactor.

A capacitor, whose capacity changes corresponding to the deposited quantity of oil particles, is advantageously provided as an evaluating means. The capacitor is advantageously arranged directly in the area of the gas jet exiting from the micronozzle. The capacitor may be the frequency-determining component of an oscillatory circuit, so that the deposited quantity of oil can be determined by determining the frequency.

Alternative evaluating means are a capillary, which absorbs the oil, or an electrode array, with which the change in conductivity based on the deposited quantity of oil is determined, or optical image converters, e.g., in the form of a CCD chip.

The method according to the present invention for the selective determination of the quantity of oil mist in a gas sample uses a predetermined volume of gas to be tested with this being dispensed with the micronozzle. This allows oil particles to be deposited on the baffle plate arranged downstream of the micronozzle. Such a deposit occurs according to the impactor principle. The deposited quantity of oil particles can be determined via a window on the side of the baffle plate facing away from the micronozzle.

An exemplary embodiment of the present invention is shown in the figures and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
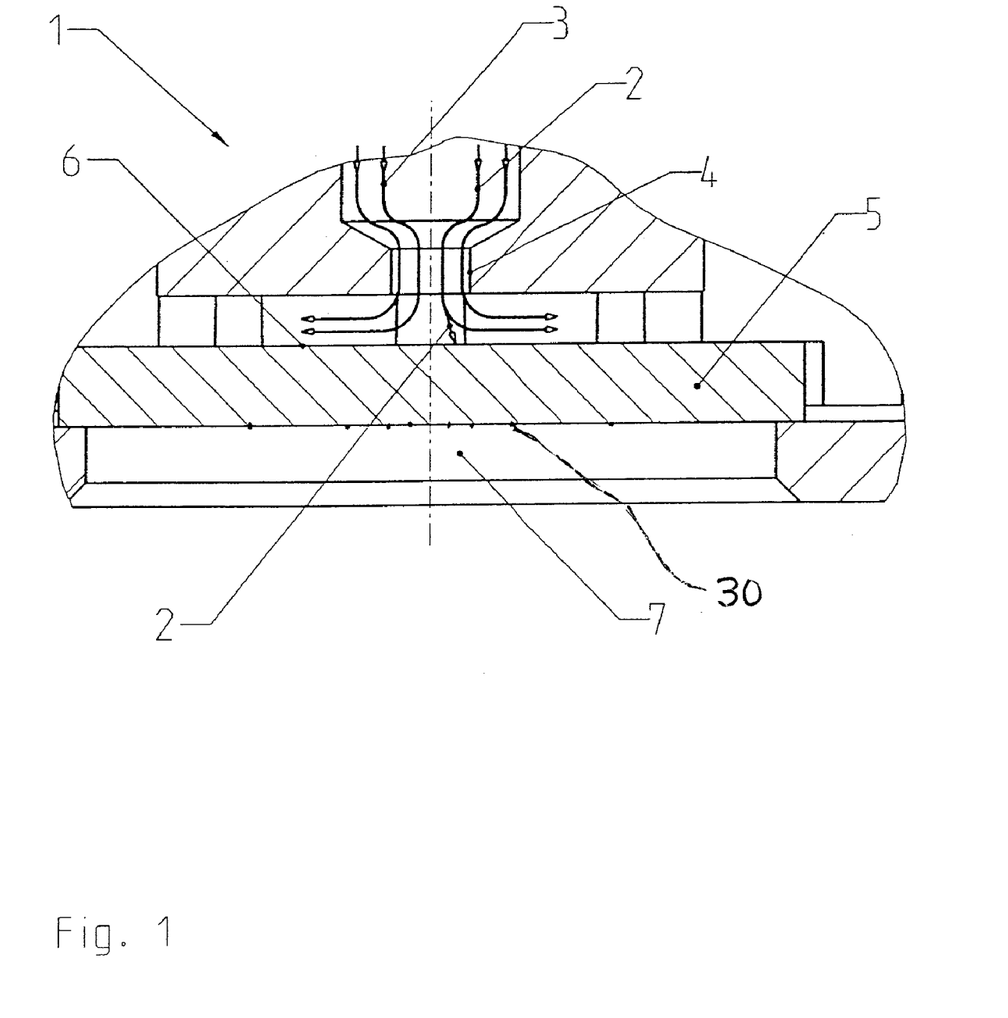
FIG. 1 is a schematic view showing the design of an impactor according to the invention.

Referring to the drawings in particular, FIG. 1 schematically illustrates the design of an impactor 1 for the selective measurement of the quantity of oil mist in a gas to be tested. The gas 3, which is loaded with oil particles 2 and is coming from a gas source, not shown, flows through a micronozzle 4 and is deflected at a transparent baffle plate 5 at right angles to the direction in which it enters. Because of the abruptly changing direction of flow, the oil particles 2 are no longer able to follow the flow and are deposited on an absorbent material 6 on the baffle plate 5. The oil particles that impact the baffle plate 5 are collected on the material 6. An oil spot, whose size is perceptible via a window (opening) 7, is now formed on the material 6. The diameter of the oil spot is an indicator of the quantity of deposited oil aerosol. This may be observed based on a scale 30 perceptible via a window (opening) 7 with the plate 5 being glass such as frosted glass.

When the measurement is carried out, the concentration of oil aerosol that is tested is set at first, i.e., for example, the limit value in the breathing air for divers, equaling 0.5 mg per $m^3$ or 0.5 μg per L. At this concentration, 0.5 μg per minute would already be deposited at a gas flow of 1 L per minute. Consequently, one would have a precalibrated standard spot of 5 μL of oil after 5 minutes. If the spot is smaller than the standard spot, the limit value is not reached. If other concentrations are to be measured, the measurement time must be correspondingly adapted. The measurement time must be 25 minutes at a limit value of 0.1 μg per L for compressed air in hospitals. A mark is made for this for the standard spot or "oil spot visible or not visible" is taken as the criterion. The advantage of taking the visibility limit of the oil spot as a criterion is very short measurement times. However, the result depends more strongly on the user or the user's visual acuity.

An alternative possibility is to specify a fixed measurement time and to provide a scale within the window 7, with which the diameter of the oil spot can be determined.

Figure 2:
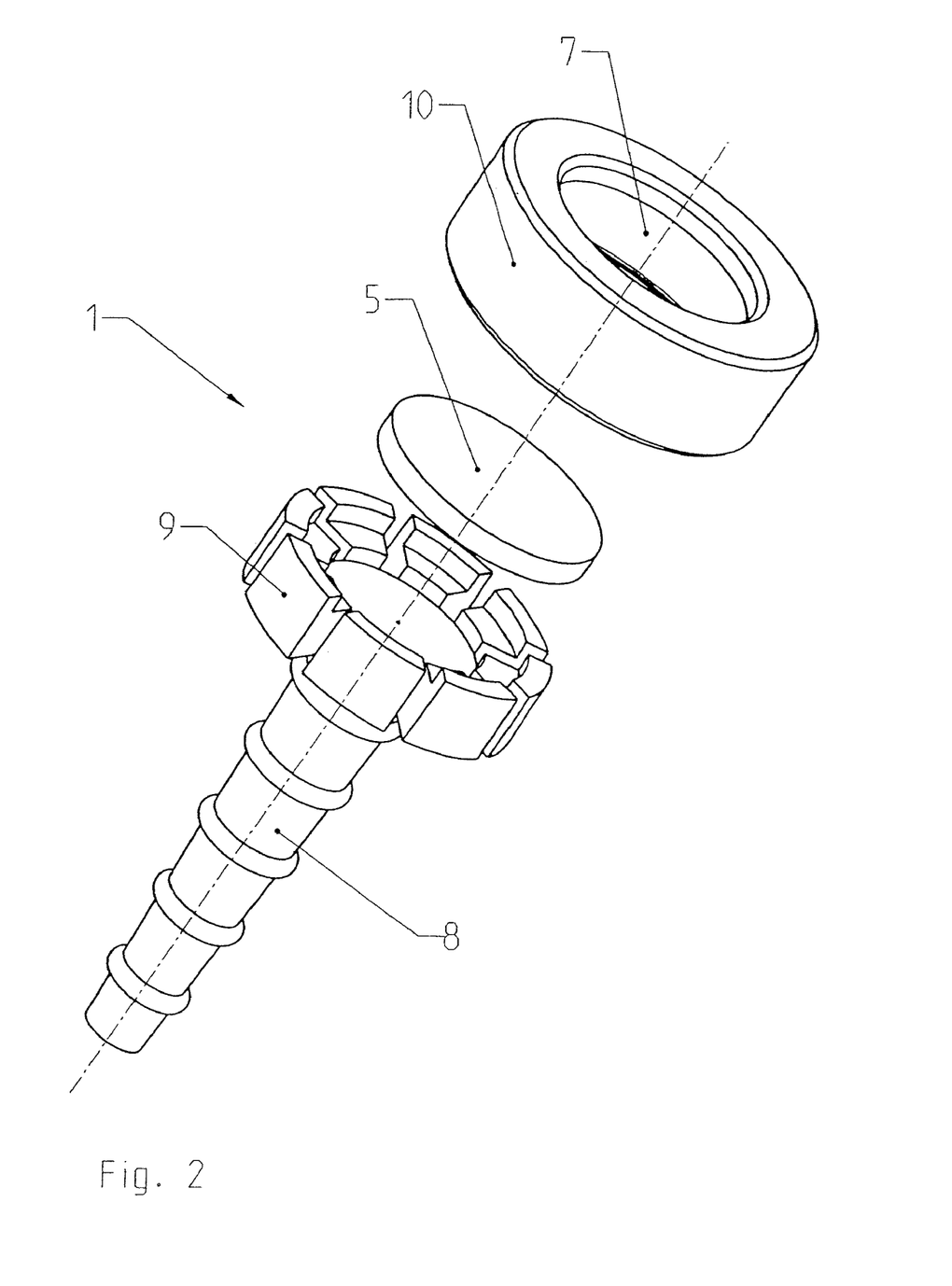
FIG. 2 is an exploded perspective view of the impactor.

FIG. 2 shows a perspective exploded view of the impactor 1 corresponding to FIG. 1 with a connection 8 for the gas to be tested. The impactor 1 comprises an impactor housing 9 and a snap ring 10 with the window 7, the baffle plate 5 being fixed on the impactor housing 9 with the snap ring 10.

Figure 3:
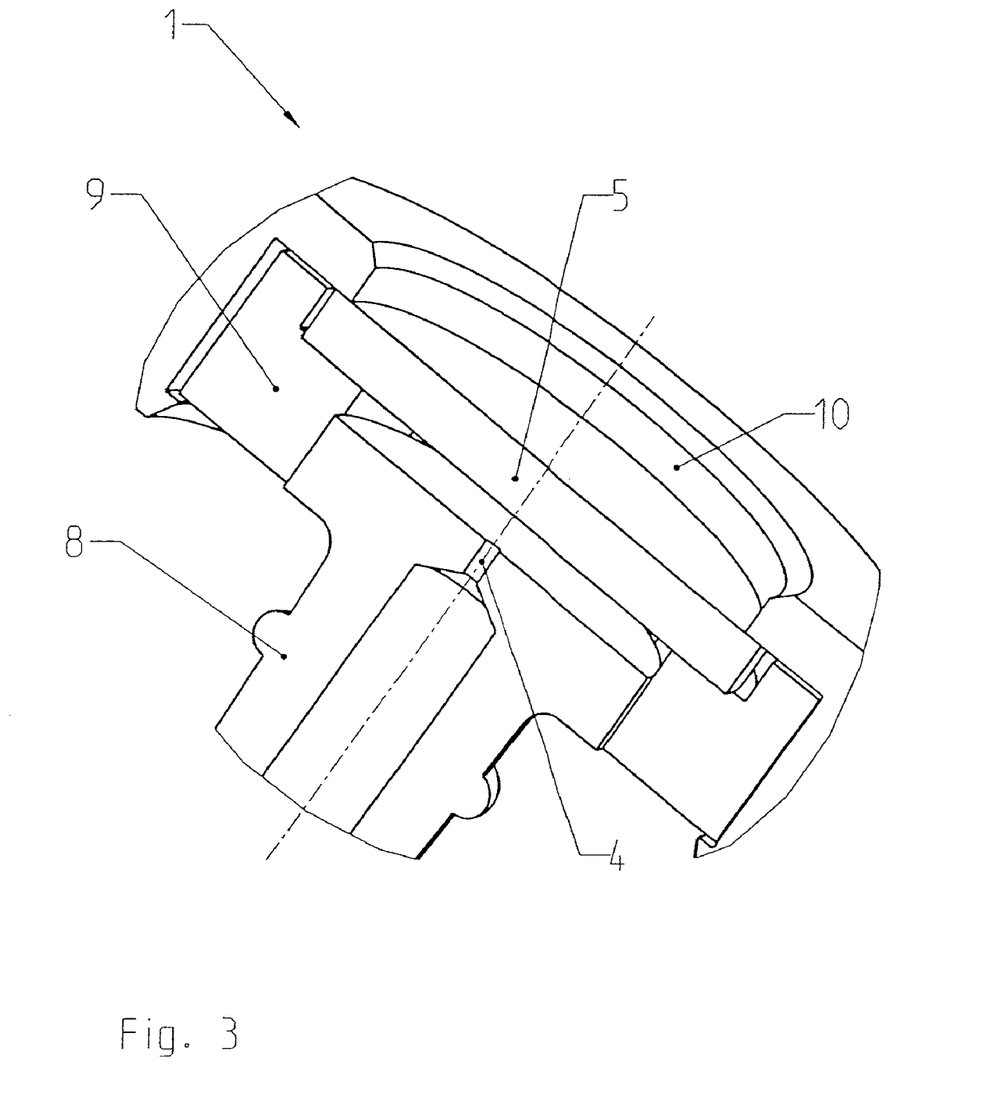
FIG. 3 is a longitudinal sectional view of the impactor according to FIG. 2.

FIG. 3 shows the longitudinal section of the impactor 1 according to FIG. 2. Identical components are designated by the same reference numbers as in FIGS. 1 and 2. The micronozzle 4 has a diameter of 127 μm in the embodiment shown in FIGS. 2 and 3.

Figure 4A:
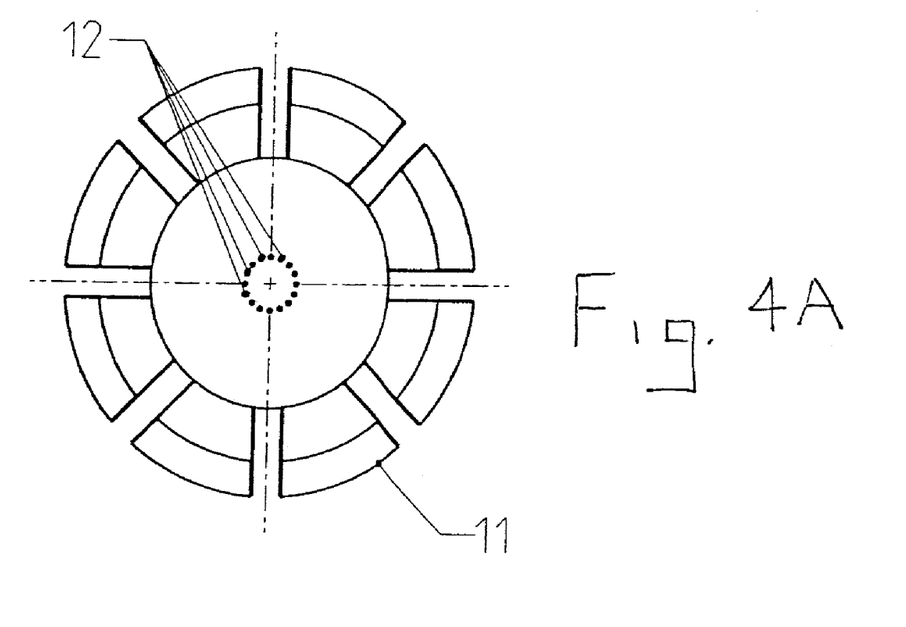
FIG. 4A is a end/top view of an alternative impactor housing.
Figure 4B:
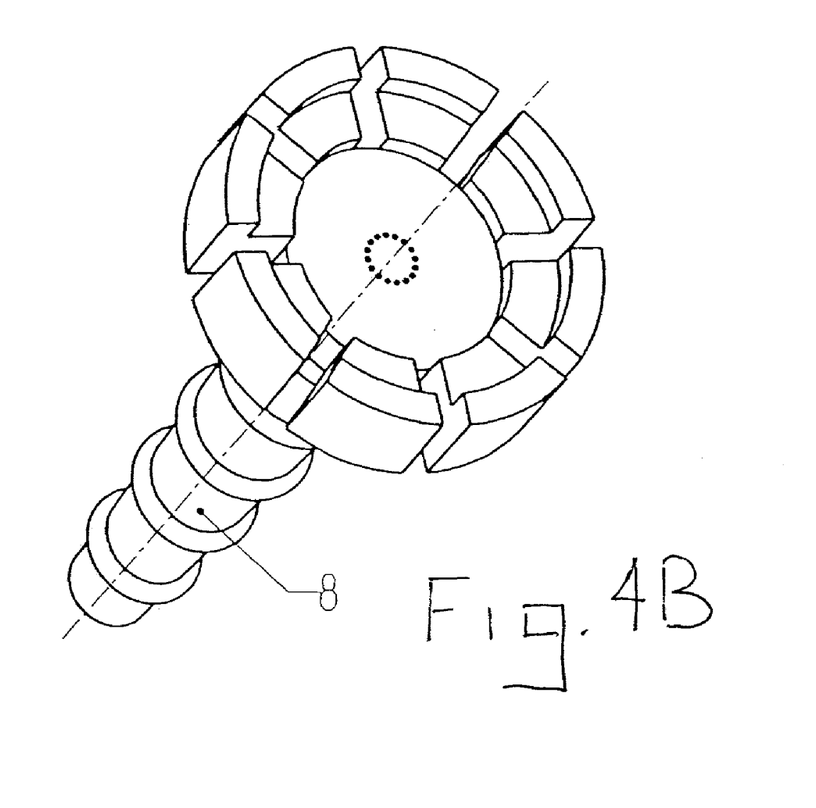
FIG. 4B is a top perspective view of the impactor housing of FIG. 4A.

FIGS. 4A and 4B respectively show a top view and perspective of an alternative impactor housing 11. The impactor housing 11 forms a plurality of micronozzles 12 that are arranged in a circular pattern instead of a centrally arranged impactor nozzle 4 corresponding to FIG. 3. The distances between two micronozzles 12 are selected in the form of a threshold value calibration such that it is determined, relative to a predetermined measurement time, whether a plurality of oil spots produced by the micronozzles 12 have merged into a large oil spot.

Figure 5:
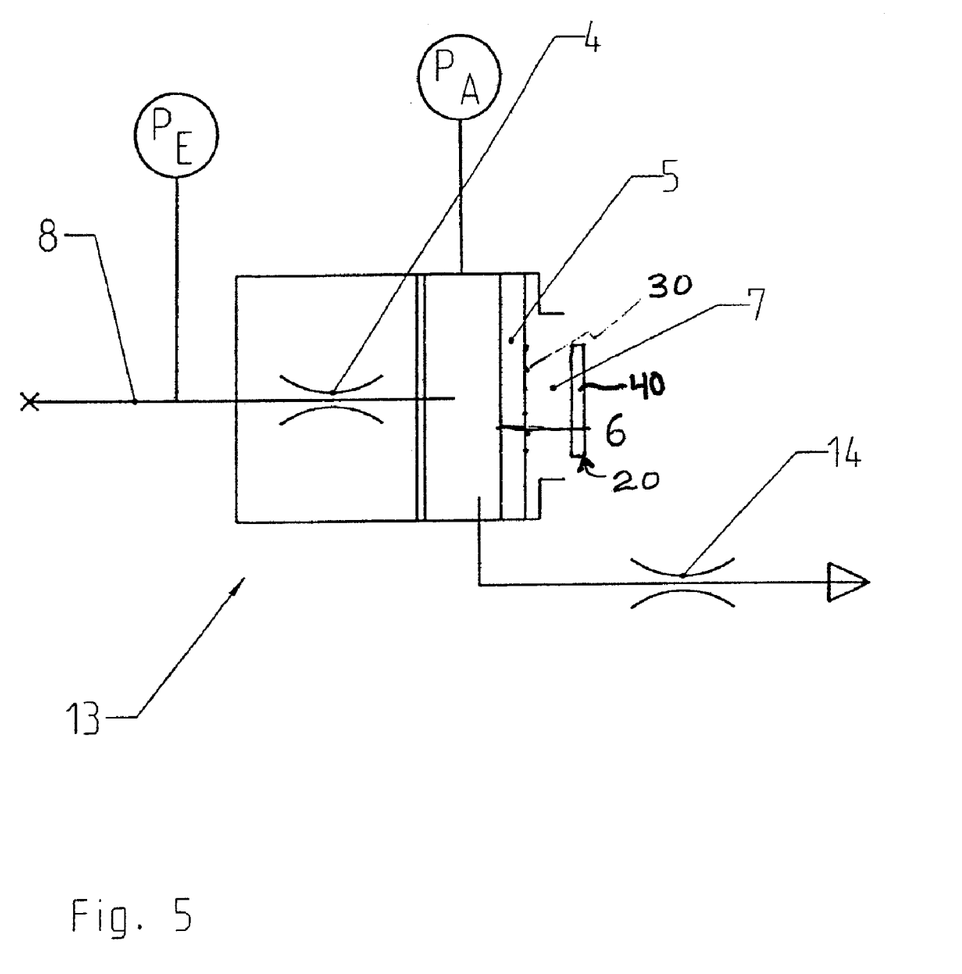
FIG. 5 is a schematic view of the impactor system with a nozzle (flow restriction/throttle) arranged downstream of the baffle plate.

FIG. 5 schematically illustrates an alternative embodiment of an impactor 13, in which the gas to be tested flows off behind the micronozzle 4 via a critical nozzle (flow restriction/throttle) 14 arranged downstream. With this the system includes the features of either the embodiment of FIG. 2 or 4a/4B. Identical components are designated by the same reference numbers as in FIGS. 2 and 3. Further the flow of gas downstream of the point of impact with baffle plate 5 is channeled so as to proceed via the critical nozzle (flow restriction/throttle) 14.

The arrangement of a separate critical nozzle (flow restriction/throttle) 14 downstream is advantageous for the following reasons. The impactor housing 9 is preferably manufactured as a disposable part for cost reasons. Since the micronozzle 4 determines the gas to be tested flow, it must be manufactured with high precision, which increases the production costs. The critical nozzle (flow restriction/throttle) 14 arranged downstream has nearly unlimited reusability and may be a fixed component of a testing means, which is not shown in more detail in FIG. 5. When the micronozzle 4 is used without a nozzle (flow restriction/throttle) 14 arranged downstream in the supercritical range, the gas jet 3 expands behind the micronozzle 4, which may lead to lower deposition performance. The arrangement of a critical nozzle 14 downstream, which is proposed according to the present invention, prevents supercritical operation and brings about a constant pressure drop over the micronozzle 4. FIG. 5 also shows the evaluating means including the transparent/opaque plate 5, an absorbent material 6 and a scale 30 provided in the area of the window (opening) 7 for determining an aerosol limit value. As a further feature of the evaluating means a detector 20 may be provided. The detector 20 may include a capacitor which changes its capacitance due to the oil particles present on the plate 5 or on the absorbent material 6. In this case the plate 5 need not be transparent/opaque. In this case the detector 20 includes an electric oscillatory circuit 40 with the capacitor being a frequency-determining component thereof. The detector 20 may include a capillary receiving the oil (this may be the absorbent material 6 cooperating with transparent/opaque plate 5), an electrode array for conductivity measurement, or an optical image converter in the form of a CCD chip.

Figure 6:
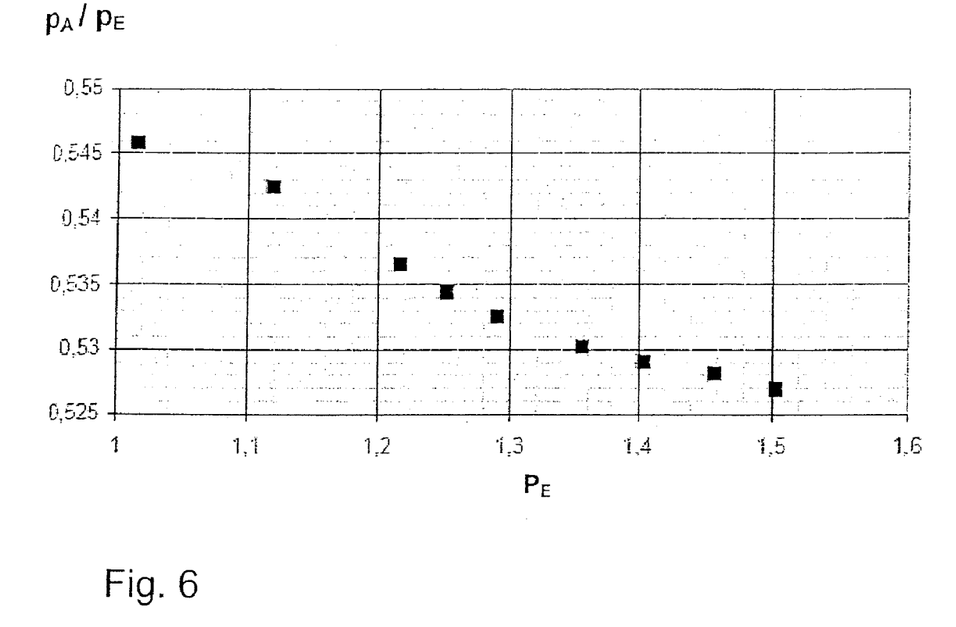
FIG. 6 is a diagram showing the pressure ratio over the micronozzle of an impactor with a nozzle (flow restriction/throttle) arranged downstream.

FIG. 6 shows the pressure ratio $p_A/p_E$ over the micronozzle 4 with the critical nozzle (flow restriction/throttle) 14 arranged downstream as a function of the inlet pressure $p_E$ (bar). Corresponding to FIG. 5, $p_A$ is the pressure at the outlet of the micronozzle 4. The pressure at the outlet of the critical nozzle 14 equals 0.2 bar. If, for example, the inlet pressure $p_E$ in front of the micronozzle 4 is increased by 50%, for example, from 1 bar to 1.5 bar, the pressure ratio $p_A/p_E$ decreases by less than 4%.

While specific embodiments of the invention have been shown and described in detail to illustrate the application of the principles of the invention, it will be understood that the invention may be embodied otherwise without departing from such principles.

What is claimed is:

1. A device for the selective determination of the quantity of oil mist in a gas sample, the device comprising:
   an impactor with a micronozzle for dispensing a predetermined volume of gas to be tested;
   a baffle plate downstream of said micronozzle for depositing oil particles from the sample; and
   an evaluating means for evaluating oil deposited in the area of said baffle plate, said evaluating means comprising a viewing region on a side of said baffle plate facing away from said micronozzle, said baffle plate being opaque or transparent, said evaluating means including a scale provided in an area of said viewing region for determining an aerosol limit value.

2. A device in accordance with claim 1, wherein said baffle plate is provided with an absorbent material downstream of said micronozzle, said evaluating means including said absorbent material.

3. A device in accordance with claim 1, further comprising additional micronozzles cooperating with said micronozzle to provide a plurality of said micronozzles arranged in a predetermined pattern.

4. A device in accordance with claim 3, wherein the predetermined pattern is a circle, a square, a rectangle, a triangle, a symbol or a letter.

5. A device in accordance with claim 1, further comprising a critical nozzle arranged downstream of said micronozzle of said impactor.

6. A device in accordance with claim 1, wherein said evaluating means is a capillary receiving the oil, an electrode array for conductivity measurement, or an optical image converter in the form of a CCD chip.

7. A method for the selective determination of a quantity of oil mist in a gas sample, the method comprising:
   dispensing a predetermined volume of gas to be tested with a micronozzle;
   depositing oil particles on a baffle plate arranged downstream of said micronozzle according to the impactor principle; and
   determining a quantity of deposited oil particles with an evaluating device in an area of said baffle plate, said evaluating device comprising a viewing region on a side of said baffle plate facing away from said micronozzle, said plate being one of opaque and transparent said evaluating device including a scale provided in an area of said viewing region for determining an aerosol limit value.

8. A gas sample oil mist determination system comprising:
   an impactor body defining a micronozzle for dispensing gas to be tested;
   a plate downstream of said micronozzle for receiving oil particles from the gas sample upon the gas sample impacting said plate; and
   an evaluating means for facilitating an evaluation of oil deposited in an area of said plate facing away from the gas impacting said plate, said evaluating means comprising a viewing region on a side of said plate facing away from said micronozzle, said plate being one of opaque and transparent, said evaluating means including absorbent material as part of said plate or provided on said plate and a scale provided in an area of said viewing region for determining an aerosol limit value.

9. A system in accordance with claim 8, further comprising additional micronozzles cooperating with said micronozzle to provide a plurality of said micronozzles arranged in a predetermined pattern.

10. A system in accordance with claim 8, further comprising:
    a downstream flow path leading gas away from said plate after the gas has impacted said plate; and
    a flow restriction arranged along said downstream flow path.

11. A system in accordance with claim 8, wherein said evaluating means comprises a capillary receiving the oil, an electrode array for conductivity measurement, or an optical image converter in the form of a CCD chip.

* * * * *